(12) United States Patent
Wang et al.

(10) Patent No.: US 12,048,498 B2
(45) Date of Patent: Jul. 30, 2024

(54) BI-PLANAR ROBOTIC ARM DEVICE FOR VASCULAR INTERVENTIONAL SURGERY

(71) Applicant: SHANGHAI OPERATION ROBOT CO., LTD., Shanghai (CN)

(72) Inventors: Kundong Wang, Shanghai (CN); Qingsheng Lu, Shanghai (CN); Meng Li, Shanghai (CN); Liangle Zhu, Shanghai (CN); Daozhi Liu, Shanghai (CN); Yikun Liu, Shanghai (CN); Zhongwei Yu, Shanghai (CN)

(73) Assignee: SHANGHAI OPERATION ROBOT CO., LTD., Shanghai (CN)

( * ) Notice: Subject to any disclaimer, the term of this patent is extended or adjusted under 35 U.S.C. 154(b) by 32 days.

(21) Appl. No.: 17/912,506

(22) PCT Filed: Apr. 7, 2020

(86) PCT No.: PCT/CN2020/083459
§ 371 (c)(1),
(2) Date: Sep. 17, 2022

(87) PCT Pub. No.: WO2021/184444
PCT Pub. Date: Sep. 23, 2021

(65) Prior Publication Data
US 2023/0141650 A1 May 11, 2023

(30) Foreign Application Priority Data
Mar. 17, 2020 (CN) .......................... 202010187837.7

(51) Int. Cl.
*A61B 34/30* (2016.01)
(52) U.S. Cl.
CPC ........ *A61B 34/30* (2016.02); *A61B 2034/301* (2016.02)

(58) Field of Classification Search
CPC .............. A61B 34/30; A61B 2034/301; A61B 2090/571; A61B 34/37; A61B 34/70; A61B 2034/303; A61B 2034/305; Y02A 50/30
See application file for complete search history.

(56) References Cited

U.S. PATENT DOCUMENTS 9,193,573 B1 * 11/2015 Troy ........................ B66F 7/065
2002/0111634 A1 8/2002 Stoianovici et al.
(Continued)

FOREIGN PATENT DOCUMENTS

CN 202143653 U 2/2012
CN 105650547 A 6/2016
(Continued)

OTHER PUBLICATIONS

English Translation of WO-2016046089-A1 (Year: 2016).*

*Primary Examiner* — Victor L MacArthur
(74) *Attorney, Agent, or Firm* — Bayramoglu Law Offices LLC

(57) ABSTRACT

A bi-planar robotic arm device for vascular interventional surgery includes an operating table, a frame assembly, an outer arm assembly, and an inner arm assembly. The frame assembly includes a standing column, a sliding block, a sliding platform, a support, and a screw stepper motor. The standing column is arranged on the operating table. The support is arranged on the standing column. The sliding platform is arranged on the support. The sliding platform is connected to the sliding block. The sliding block is connected to the screw stepper motor and can slide along the sliding platform under the action of the screw stepper motor. The outer arm assembly is connected to the standing column. The inner arm assembly is connected to the outer arm (Continued)

assembly and the sliding block. The inner arm assembly and the outer arm assembly can move relative to each other.

10 Claims, 2 Drawing Sheets

(56) References Cited

U.S. PATENT DOCUMENTS

| | | |
|---|---|---|
| 2017/0112576 A1 | 4/2017 | Coste-Maniere et al. |
| 2019/0083183 A1 | 3/2019 | Moll et al. |
| 2019/0192244 A1 | 6/2019 | Mirbagheri et al. |

FOREIGN PATENT DOCUMENTS

| | | | |
|---|---|---|---|
| CN | 205598007 U | 9/2016 | |
| CN | 107049500 A | 8/2017 | |
| CN | 108557450 A | 9/2018 | |
| CN | 108670413 A | 10/2018 | |
| CN | 108938363 A | 12/2018 | |
| CN | 109157729 A | 1/2019 | |
| CN | 109199590 A | 1/2019 | |
| CN | 109288589 A | 2/2019 | |
| CN | 109288593 A | 2/2019 | |
| CN | 209755205 U | 12/2019 | |
| JP | 6546361 B1 | 7/2019 | |
| WO | WO-2016046089 A1 * | 3/2016 | ............ A61B 17/64 |
| WO | 2018216382 A1 | 11/2018 | |
| WO | 2019143458 A1 | 7/2019 | |

* cited by examiner ns of surgeons are diverse, involving speed, strength, position, and so on, but the roller push mechanism lacks the necessary flexibility. The flexibility requires the cooperation of multiple interventional devices and a large dynamic movement range of the devices. It is desirable that a solution based on using a robot arm is able to meet the flexibility requirement. In practice, the surgeon generally uses both hands to clamp and twist the catheter/guidewire and cooperatively uses the two arms to achieve the advance, retreat, and cooperation of the catheter/guidewire, as well as the distal operation. For this reason, the present invention provides a solution, in which a bi-planar robotic arm for vascular intervention is designed to simulate the two arms of the surgeon. The bi-planar robotic arm can realize straight (e.g., linear) pushing/pulling and meet the operational requirements in a large dynamic range.

BI-PLANAR ROBOTIC ARM DEVICE FOR VASCULAR INTERVENTIONAL SURGERY

CROSS REFERENCES TO THE RELATED APPLICATIONS

The application is the national phase entry of International Application No. PCT/CN2020/083459, filed on Apr. 7, 2020, which is based on and claims priority on Chinese patent application No. 202010187837.7, filed on Mar. 17, 2020, the entire contents of which are incorporated herein by reference.

TECHNICAL FIELD

The present invention relates to the field of medical devices, in particular, a bi-planar robotic arm device for vascular interventional surgery.

BACKGROUND

A vascular interventional surgery robot generally works in the master-slave teleoperation mode, which can prevent the surgeon from the cumulative radiation damage caused by the long-term use of the digital subtraction angiography (DSA) instrument. More importantly, the master-slave operation can improve the accuracy and stability of the operation, prevent the surgeon from becoming fatigued, and improve the quality of interventional surgery. The master of the robot is the surgeon, which is typically achieved by the handle operation instruction from the surgeon, including clamping, rotation, and pushing/pulling, as well as the combination of these actions. Among them, the pushing/pulling manipulation of the catheter/guidewire is the most basic and frequent action, including pulling out the catheter/guidewire along a straight path as much as possible along the exit direction of the sheath and segmentally pushing the catheter/guidewire along a straight path from the opening of the sheath. Because some of the existing catheters/guidewires are up to 2.5 meters long and complex surgery needs to simultaneously use several catheters/guidewires, the interventional device is required to push a larger working range and has more push points.

At present, the traditional method for pushing and pulling the guidewire/catheter of the robot for vascular intervention surgery is to use two rollers to press the catheter or guidewire, and then the rollers roll forward to make the catheter or guidewire move forward or the rollers roll reversely to make the catheter/guidewire retreat, such as the products of Catheter Robotics company of France and CorPath company of the United States. Although this method can effectively control the advance and retreat of catheters/guidewires, it is difficult to realize the large-scale coaxial operation of multiple catheters/guidewires. In China, this problem also exists in the method proposed by the Institute of Automation of the Chinese Academy of Sciences, in which the rollers roll to clamp and push the catheter/guidewire, and the method proposed by Beijing Institute of Technology, in which gears force out, clamp, and push the catheter/guidewire.

The surgical robot pursues the transparency of the operation, that is, the manipulations of the surgeon is replicated by the slave robotic arm of the surgical robot as closely as possible. The roller forces out the catheter/guidewire and pushes the catheter/guidewire to realize the push operation of the catheter/guidewire, but the rollers implement the movement function rather than reproduce the manipulation The Chinese patent No. CN109157729A discloses a guidewire delivery device for vascular interventional surgery, including a support part, where the driving device is arranged on the supporting part. The driving device is connected to an active motion device, and a plurality of connecting rods are arranged on the active motion device. One end of the connecting rod is hinged with the active motion device, and the other end of the connecting rod is hinged with a guidewire clamping device. The guidewire clamping device is slidably connected to a guiding device, which is fixedly connected to a connecting frame, and the connecting frame is arranged on the supporting part. The guidewire delivery device has a small size, good transmission precision of the whole mechanism, convenient handling, high efficiency of delivering the guidewire, lower labor intensity of the surgeon, and high practicability, which is worth popularizing. However, this method can only effectively control the advance and retreat of the catheter/guidewire; it is difficult to achieve a wide range of coaxial operation of multiple catheters/guidewires, and thus, cannot achieve the identical reproduction of the surgeon's manipulations.

SUMMARY

In view of the defects in the prior art, the object of the invention is to provide a bi-planar robotic arm device for vascular interventional surgery.

A bi-planar robotic arm device for vascular interventional surgery includes an operating table, a frame assembly, an outer arm assembly, and an inner arm assembly. The frame assembly includes a standing column, a sliding block, a sliding platform, a support, and a screw stepper motor.

The standing column is arranged on the operating table. The support is arranged on the standing column. The sliding platform is arranged on the support. The sliding platform is connected to the sliding block. The sliding block is connected to the screw stepper motor and can slide along the sliding platform under the action of the screw stepper motor.

The outer arm assembly is connected to the standing column. The inner arm assembly is connected to the outer arm assembly and the sliding block. The inner arm assembly and the outer arm assembly can move relative to each other.

Preferably, the outer arm assembly includes an outer arm first motor, a transmission shaft, an outer arm first connecting rod, an outer arm second motor, an outer arm second connecting rod, an outer arm third motor, and an outer arm third connecting rod.

The outer arm first motor is arranged on the standing column. The outer arm first motor is connected to one end of the outer arm first connecting rod through the transmission shaft. The other end of the outer arm first connecting rod is connected to one end of the outer arm second connecting rod. The other end of the outer arm second connecting rod is connected to one end of the outer arm third connecting rod. The other end of the outer arm third connecting rod is the clamping end. The outer arm second motor is arranged at one end of the outer arm second connecting rod. The outer arm third motor is arranged at one end of the outer arm third connecting rod.

Preferably, the inner arm assembly includes an inner arm first motor, a transmission assembly, a transmission cylinder, a supporting bearing assembly, an inner arm first connecting rod, an inner arm second motor, an inner arm second connecting rod, an inner arm third motor, and an inner arm third connecting rod.

The inner arm first motor is arranged on the sliding block. The inner arm first motor is connected to the transmission cylinder through the transmission assembly. The transmission cylinder is connected to one end of the inner arm first connecting rod. The other end of the inner arm first connecting rod is connected to one end of the inner arm second connecting rod. The other end of the inner arm second connecting rod is connected to one end of the inner arm third connecting rod. The other end of the inner arm third connecting rod is the clamping end. The inner arm second motor is arranged at one end of the inner arm second connecting rod. The inner arm third motor is arranged at one end of the inner arm third connecting rod.

The transmission cylinder is connected to the sliding block through the supporting bearing assembly. The transmission cylinder is hollow, and the transmission shaft of the outer arm assembly passes through the transmission cylinder.

Preferably, the transmission assembly includes a driving pulley, a belt, and a driven pulley. The driving pulley is connected to the inner arm first motor. The driven pulley is coaxially arranged on the transmission cylinder, and the driving pulley is connected to the driven pulley through the belt.

Preferably, the transmission cylinder coincides with the axis of the transmission shaft of the outer arm assembly, and the transmission cylinder and the transmission shaft of the outer arm assembly can slide and rotate relative along the axis.

Preferably, the transmission shaft is a telescopic rod.

Preferably, the transmission shaft rotates under the action of the outer arm first motor, thereby driving the outer arm first connecting rod to rotate. The outer arm first connecting rod is rotatably connected to the outer arm second connecting rod. The outer arm second connecting rod can rotate relative to the outer arm first connecting rod under the action of the outer arm second motor. The outer arm second connecting rod is rotatably connected to the outer arm third connecting rod. The outer arm third connecting rod can rotate relative to the outer arm second connecting rod under the action of the outer arm third motor.

The rotation axis of the outer arm first connecting rod, the rotation axis of the outer arm second connecting rod, and the rotation axis of the outer arm third connecting rod are parallel to each other.

The outer arm first connecting rod, the outer arm second connecting rod, and the outer arm third connecting rod are located in the same plane.

Preferably, the transmission cylinder rotates under the action of the inner arm first motor and the transmission assembly, thereby driving the inner arm first connecting rod to rotate. The inner arm first connecting rod is rotatably connected to the inner arm second connecting rod. The inner arm second connecting rod can rotate relative to the inner arm first connecting rod under the action of the inner arm second motor. The inner arm second connecting rod is rotatably connected to the inner arm third connecting rod. The inner arm third connecting rod can rotate relative to the inner arm second connecting rod under the action of the inner arm third motor.

The rotation axis of the inner arm first connecting rod, the rotation axis of the inner arm second connecting rod, and the rotation axis of the inner arm third connecting rod are parallel to each other.

The inner arm first connecting rod, the inner arm second connecting rod, and the inner arm third connecting rod are located in the same plane.

Preferably, the motion plane of the outer arm first connecting rod, the outer arm second connecting rod, and the outer arm third connecting rod of the outer arm assembly is parallel to the motion plane of the inner arm first connecting rod, the inner arm second connecting rod and the inner arm third connecting rod of the inner arm assembly.

Preferably, the bi-planar robotic arm device further includes a controller. The controller is connected to the transmission shaft, the screw stepper motor, the outer arm first motor, the outer arm second motor, the outer arm third motor of the outer arm assembly, and the inner arm first motor, the inner arm second motor, the inner arm third motor of the inner arm assembly with signals.

Compared with the prior art, the present invention has the following beneficial effects:

1. Based on the bionics principle, the present invention realizes the linear pushing/pulling motion of the catheter/guidewire through a three-degree of freedom (3 DoF) robotic arm. The robotic arms have a large motion range, which solves the problems of insufficient motion range, flexibility, and maneuverability inherent in the existing mechanism and meets the needs of clinical application.
2. The robotic arms of the present invention are located in two parallel planes, and the distance between the two planes of the robotic arms can be changed through the sliding platform to meet the needs of interventional surgery in peripheral vascular diseases, cardiovascular diseases, nervous system diseases, etc.
3. The motions of the two robotic arms of the present invention are independently controlled and do not interfere with each other. The motion parameters of the robotic arms can be obtained by inverse kinematics solution according to the position and posture of the catheter/guidewire in the base coordinate system of the surgical robot. The inverse kinematics solution is fast and has a unique solution, which can solve the fast real-time operation of the catheter/guidewire. The control operation method is simple and easy.

BRIEF DESCRIPTION OF THE DRAWINGS

By reading the detailed description of the non-restrictive embodiment with reference to the following drawings, other features, purposes, and advantages of the present invention will become more obvious.

As the figure shows.

Figure 1:
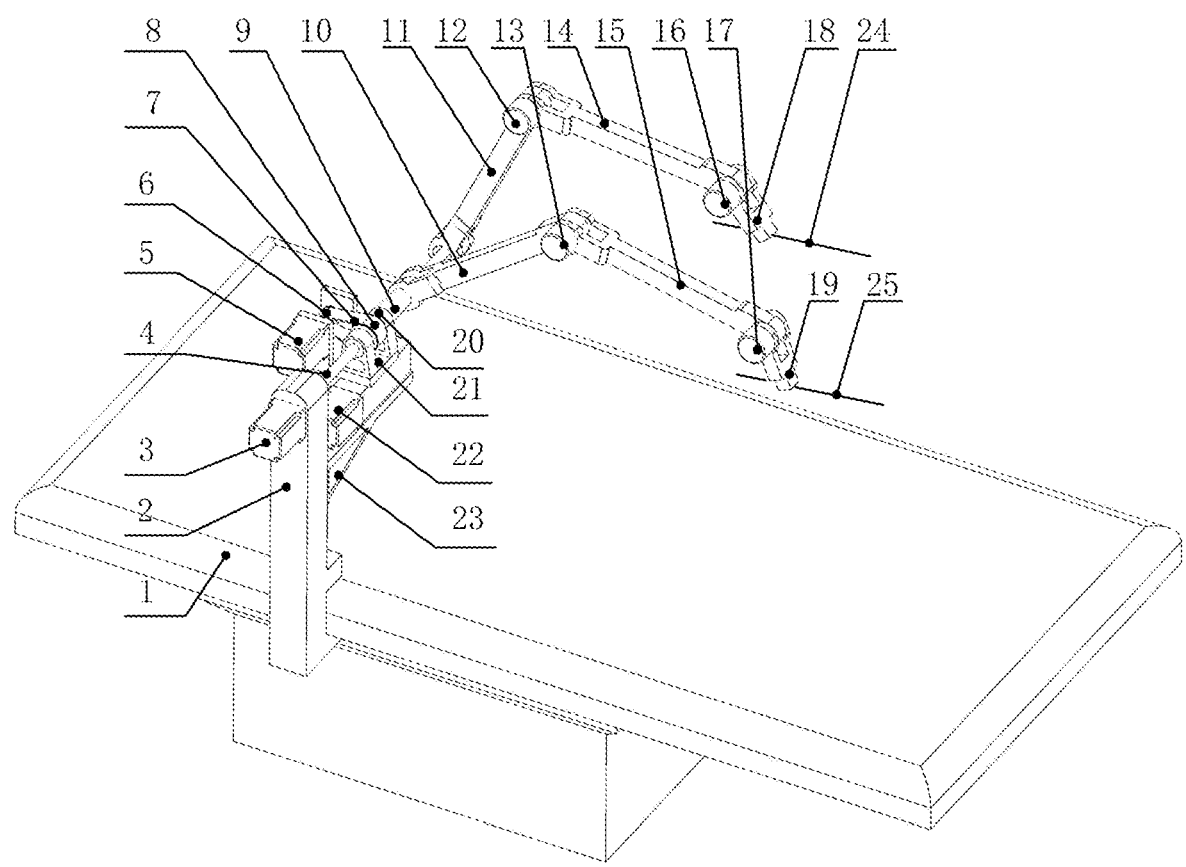
FIG. 1 shows a structural schematic diagram of the present invention.

1 -operating table
2 -standing column
3 -outer arm first motor
4 -transmission shaft
5 -inner arm first motor
6 -driving pulley
7 -belt
8 -driven pulley
9 -transmission cylinder
10 -inner arm first connecting rod
11 -outer arm third connecting rod
12 -outer arm second motor
13 -inner arm second motor
14 -outer arm second connecting rod
15 -inner arm second connecting rod
16 -outer arm third motor
17 -inner arm third motor
18 -outer arm third connecting rod
19 -inner arm third connecting rod
20 -supporting bearing assembly
21 -sliding block
22 -sliding platform
23 -support
24 - external intervention equipment
25 - internal intervention equipment

DETAILED DESCRIPTION OF THE EMBODIMENTS

The present invention is described in detail in combination with a specific embodiment. The following embodiments will help those skilled in the art to further understand the present invention but do not limit the present invention in any form. It should be noted that for ordinary technicians in the art, a number of changes and improvements can be made without departing from the idea of the present invention. These changes and improvements all belong to the protection scope of the invention.

In the description of this application, it is necessary to understand that the terms "up", "down", "front", "back", "left", "right", "vertical", "horizontal", "top", "bottom", "inside", and "outside" indicating the orientation or position are based on the orientation or position relationship shown in the attached drawings, which are only for the convenience of describing the present invention and simplifying the description, rather than indicating or implying that the device or element referred to must have a specific orientation and be constructed and operated in a specific direction. These terms cannot be understood as a restriction on this application.

The present invention provides a bi-planar robotic arm device for vascular interventional surgery, in particular, a device for linear pushing and pulling of catheter/guidewire by using planar robotic arms serially installed with three-degree of freedom (3 DoF) rotating joints, which solves the problem of linear operation of catheter/guidewire in a large range of motion. The bi-planar robotic arm device includes two robotic arms connected in serial by 3 DoF rotating joints. The shoulder joints of the two robotic arms are installed coaxially, and the width between the shoulder joints is adjusted by a translational joint, that is, the rotation axis of the outer arm first connecting rod 11 is coaxial with that of the inner arm first connecting rod 10. The ends (clamping ends) of the two robotic arms can be used for the parallel straight moving operation of the interventional device and simultaneously operate to make two groups of interventional devices move linearly. The present invention has the characteristics of large movement range, small space use, good mobility and flexibility, and can meet the needs of clinical pushing/pulling operation of interventional devices used in peripheral vascular interventional surgery, cardiovascular interventional surgery, and the like.

According to the present invention, a bi-planar robotic arm device for vascular interventional surgery, as shown in FIG. 1, includes an operating table 1, a frame assembly, an outer arm assembly, and an inner arm assembly. The frame assembly includes a standing column 2, a sliding block 21, a sliding platform 22, a support 23, and a screw stepper motor. The standing column 2 is arranged on the operating table 1. The support 23 is arranged on the standing column 2. The sliding platform 22 is arranged on the support 23. The sliding platform 22 is connected to the sliding block 21. The sliding block 21 is connected to the screw stepper motor and can slide along the sliding platform 22 under the action of the screw stepper motor. The outer arm assembly is connected to the standing column 2. The inner arm assembly is connected to the outer arm assembly and the sliding block 21. The inner arm assembly and the outer arm assembly can move relative to each other. Preferably, the standing column 2 is mounted on the side of the operating table 1, and the inner arm assembly is installed on the sliding block 21 to be translated synchronously.

The outer arm assembly includes an outer arm first motor 3, a transmission shaft 4, an outer arm first connecting rod 11, an outer arm second motor 12, an outer arm second connecting rod 14, an outer arm third motor 16, and an outer arm third connecting rod 18. The outer arm first motor 3 is arranged on the standing column 2. The outer arm first motor 3 is connected to one end of the outer arm first connecting rod 11 through the transmission shaft 4. The other end of the outer arm first connecting rod 11 is connected to one end of the outer arm second connecting rod 14. The other end of the outer arm second connecting rod 14 is connected to one end of the outer arm third connecting rod 18. The other end of the outer arm third connecting rod 18 is the clamping end. The outer arm second motor 12 is arranged at one end of the outer arm second connecting rod 14. The outer arm third motor 16 is arranged at one end of the outer arm third connecting rod 18. The clamping end of the outer arm third connecting rod 18 can clamp the external interventional device 24 and perform a straight-line pushing/pulling operation on the interventional device in the motion plane of the outer arm assembly. The outer arm first motor 3 is arranged on the standing column 2 to reduce the weight of the outer arm assembly.

The inner arm assembly includes an inner arm first motor 5, a transmission assembly, a transmission cylinder 9, a supporting bearing assembly 20, an inner arm first connecting rod 10, an inner arm second motor 13, an inner arm second connecting rod 15, an inner arm third motor 17, and an inner arm third connecting rod 19. The inner arm first motor 5 is arranged on the sliding block 21. The inner arm first motor 5 is connected to the transmission cylinder 9 through the transmission assembly. The transmission cylinder 9 is connected to one end of the inner arm first connecting rod 10. The other end of the inner arm first connecting rod 10 is connected to one end of the inner arm second connecting rod 15. The other end of the inner arm second connecting rod 15 is connected to one end of the inner arm third connecting rod 19. The other end of the inner arm third connecting rod 19 is the clamping end. The inner arm second motor 13 is arranged at one end of the inner arm second connecting rod 15. The inner arm third motor 17 is arranged at one end of the inner arm third connecting rod 19. The transmission cylinder 9 is connected to the sliding block 21 through the supporting bearing assembly 20. The interior of the transmission cylinder 9 is hollow. The transmission shaft 4 of the outer arm assembly passes through the transmission cylinder 9. The clamping end of the inner arm third connecting rod 19 can clamp the interventional device 25 and perform a straight line pushing/pulling operation on the interventional device in the motion plane of the inner arm assembly. The transmission cylinder 9 is designed to avoid movement interference between the inner arm assembly and the outer arm assembly.

The transmission assembly includes a driving pulley 6, a belt 7, and a driven pulley 8. The driving pulley 6 is connected to the inner arm first motor 5. The driven pulley 8 is coaxially arranged on the transmission cylinder 9, and the driving pulley 6 is connected to the driven pulley 8 through the belt 7. The transmission cylinder 9 coincides with the axis of the transmission shaft 4 of the outer arm assembly. The transmission cylinder 9 and the transmission shaft 4 of the outer arm assembly can slide and rotate relative along the axis. The transmission shaft 4 is a telescopic rod. Such a design makes the rotating shaft of the outer arm first connecting rod 11 coaxial with the rotating shaft of the inner arm first connecting rod 10. The inner arm assembly is fixedly installed on the sliding block 21 by the supporting bearing assembly 20, so that the inner arm assembly can travel along the transmission shaft 4 and the distance between the motion plane of the outer arm assembly and the motion plane of the inner arm assembly can be changed to simulate the flexibility of the surgeon's hands to meet the requirements of different operations.

The transmission shaft 4 rotates under the action of the outer arm first motor 3, thereby driving the outer arm first connecting rod 11 to rotate. The outer arm first connecting rod 11 is rotatably connected to the outer arm second connecting rod 14, so that the outer arm second connecting rod 14 can rotate relative to the outer arm first connecting rod 11 under the action of the outer arm second motor 12. The outer arm second connecting rod 14 is rotatably connected to the outer arm third connecting rod 18, so that the outer arm third connecting rod 18 can rotate relative to the outer arm second connecting rod 14 under the action of the outer arm third motor 16. The rotation axes of the outer arm first connecting rod 11, the outer arm second connecting rod 14, and the outer arm third connecting rod 18 are parallel to each other. The outer arm first connecting rod 11, the outer arm second connecting rod 14, and the outer arm third connecting rod 18 are located in the same plane.

The transmission cylinder 9 rotates under the action of the inner arm first motor 5 and the transmission assembly, thereby driving the inner arm first connecting rod 10 to rotate. The inner arm first connecting rod 10 is rotatably connected to the inner arm second connecting rod 15, so that the inner arm second connecting rod 15 can rotate relative to the inner arm first connecting rod 10 under the action of the inner arm second motor 13. The inner arm second connecting rod 15 is rotatably connected to the inner arm third connecting rod 19, so that the inner arm third connecting rod 19 can rotate relative to the inner arm second connecting rod 15 under the action of the inner arm third motor 17. The rotation axes of the inner arm first connecting rod 10, the inner arm second connecting rod 15, and the inner arm third connecting rod 19 are parallel to each other. The inner arm first connecting rod 10, the inner arm second connecting rod 15, and the inner arm third connecting rod 19 are located in the same plane.

The motion plane of the outer arm first connecting rod 11, the outer arm second connecting rod 14, and the outer arm third connecting rod 18 of the outer arm assembly is parallel to the motion plane of the inner arm first connecting rod 10, the inner arm second connecting rod 15 and the inner arm third connecting rod 19 of the inner arm assembly.

The bi-planar robotic arm device further includes a controller. The controller is connected to the transmission shaft 4, the screw stepper motor, the outer arm first motor 3, the outer arm second motor 12, the outer arm third motor 16 of the outer arm assembly, and the inner arm first motor 5, the inner arm second motor 13, the inner arm third motor 17 of the inner arm assembly with signals.

The clamping ends of the 3 DoF robotic arms of the inner arm assembly and the outer arm assembly clamp the interventional material (such as catheter/guidewire). The inverse kinematics solution algorithm of the catheter/guidewire advancing along a straight line to the three joints is realized by a geometric method, that is, through the real-time position and posture of the catheter/guidewire in the base coordinate system of the surgical robot, the rotation angles of the three axes of the robotic arms are calculated. The controller adjusts the corresponding motor in real time according to the rotation angle value.

Figure 2:
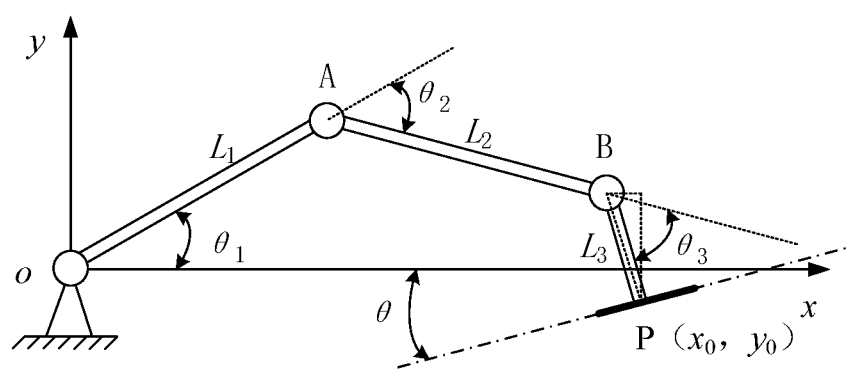
FIG. 2 shows a schematic diagram of the inverse kinematics solution of the three degrees of freedom of the planar robotic arms of the invention.

As shown in FIG. 2, the motion adjustment relationship of the 3 DoF robotic arms of the inner arm assembly and the outer arm assembly is identical. Taking the outer arm assembly as an example, taking the intersection point between the transmission shaft 4 of the outer arm assembly and the standing column 2 as the coordinate origin, the transverse motion direction of the outer arm assembly is the X axis, and the longitudinal motion direction of the outer arm assembly is the Y axis to establish a rectangular coordinate system. The length of the outer arm first connecting rod 11 is L1, the length of the outer arm second connecting rod 14 is L2, the length of the outer arm third connecting rod 18 is L3, the angle between the outer arm first connecting rod 11 and the X axis is $\theta_1$, the angle between the outer arm second connecting rod 14 and the outer arm first connecting rod 11 is $\theta_2$, and the angle between the outer arm third connecting rod 18 and the outer arm second connecting rod 14 is $\theta_3$. It is assumed that the clamping end of the robotic arm is holding the catheter/guidewire, and a typical case is that the catheter/guidewire is perpendicular to the clamping end of the robotic arms, that is, the catheter/guidewire is perpendicular to the outer arm third connecting rod 18. The inverse kinematics solution algorithm of the catheter/guidewire advancing along a straight line to the three joints is realized by the geometric method. In the x-y coordinate system (e.g., Cartesian coordinate system) shown in FIG. 2, the initial coordinate of the clamping point of the catheter/guidewire is $(x_0, y_0)$, and the angle between the catheter/guidewire and the X axis is $\theta$, then the solution relations for $\theta_1$, $\theta_2$ and $\theta_3$ are as follows:

$$x_0 = L_1 \cos\theta_1 + L_2 \cos(\theta_2 - \theta_1) + L_3 \sin\theta$$

$$y_0 = L_1 \sin\theta_1 - L_2 \sin(\theta_2 - \theta_1) - L_3 \cos\theta$$

$$\theta_1 + \theta = \theta_2 + \theta_3$$

Among them, L1, L2, L3, $\theta$, $x_0$, and $y_0$ are known, and the values of $\theta_1$, $\theta_2$, and $\theta_3$ can be calculated according to the above relationship to adjust the outer arm assembly.

Specific embodiments of the invention are described above. It should be understood that the invention is not limited to the above-mentioned specific embodiments. A person skilled in the art may make various changes or modifications within the scope of the claim, which does not affect the substance of the present invention. Without conflict, the features of the embodiments and embodiments of this application may be arbitrarily combined with each other.

What is claimed is:

1. A bi-planar robotic arm device for vascular interventional surgery comprising an operating table, a frame assembly, an outer arm assembly, and an inner arm assembly; the frame assembly comprises a standing column, a sliding block, a sliding platform, a support, and a screw stepper motor;

the standing column is arranged on the operating table, the support is arranged on the standing column, and the sliding platform is arranged on the support, and the sliding platform is connected to the sliding block, the sliding block is connected to the screw stepper motor and is allowed to slide along the sliding platform under an action of the screw stepper motor; and the outer arm assembly is connected to the standing column, and the inner arm assembly is connected to the outer arm assembly and the sliding block, and the inner arm assembly and the outer arm assembly are allowed to move relative to each other, wherein the outer arm assembly comprises an outer arm first motor, a transmission shaft, an outer arm first connecting rod, wherein the outer arm first motor is connected to a first end of the outer arm first connecting rod through the transmission shaft to move the outer arm first connecting rod via the transmission shaft, and the transmission shaft passes through the inner arm assembly such that the inner arm assembly is configured to rotate about the transmission shaft by being driven by an inner arm first motor that is different from the outer arm first motor.

2. The bi-planar robotic arm device according to claim 1, wherein the outer arm assembly comprises an outer arm second motor, an outer arm second connecting rod, an outer arm third motor, and an outer arm third connecting rod; and the outer arm first motor is arranged on the standing column, the outer arm first motor is connected to a first end of the outer arm first connecting rod through the transmission shaft, and a second end of the outer arm first connecting rod is connected to a first end of the outer arm second connecting rod, a second end of the outer arm second connecting rod is connected to a first end of the outer arm third connecting rod, a second end of the outer arm third connecting rod is a first clamping end, and the outer arm second motor is arranged at the first end of the outer arm second connecting rod; the outer arm third motor is arranged at the first end of the outer arm third connecting rod.

3. The bi-planar robotic arm device according to claim 2, wherein the transmission shaft rotates under an action of the outer arm first motor to drive the outer arm first connecting rod to rotate, the outer arm first connecting rod is rotatably connected to the outer arm second connecting rod, the outer arm second connecting rod is allowed to rotate relative to the outer arm first connecting rod under an action of the outer arm second motor, the outer arm second connecting rod is rotatably connected to the outer arm third connecting rod, and the outer arm third connecting rod is allowed to rotate relative to the outer arm second connecting rod under an action of the outer arm third motor;

a rotation axis of the outer arm first connecting rod, a rotation axis of the outer arm second connecting rod, and a rotation axis of the outer arm third connecting rod are parallel to each other; the outer arm first connecting rod, the outer arm second connecting rod, and the outer arm third connecting rod are located in a first motion plane.

4. The bi-planar robotic arm device according to claim 1, wherein a first motion plane of the outer arm first connecting rod, the outer arm second connecting rod, and the outer arm third connecting rod of the outer arm assembly is parallel to a second motion plane of the inner arm first connecting rod, the inner arm second connecting rod, and the inner arm third connecting rod of the inner arm assembly.

5. The bi-planar robotic arm device according to claim 1, further comprising a controller, wherein the controller controls the transmission shaft, the screw stepper motor, the outer arm first motor and the inner arm first motor with signals.

6. A bi-planar robotic arm device for vascular interventional surgery comprising an operating table, a frame assembly, an outer arm assembly, and an inner arm assembly; the frame assembly comprises a standing column, a sliding block, a sliding platform, a support, and a screw stepper motor;

the standing column is arranged on the operating table, the support is arranged on the standing column, and the sliding platform is arranged on the support, and the sliding platform is connected to the sliding block, the sliding block is connected to the screw stepper motor and is allowed to slide along the sliding platform under an action of the screw stepper motor; and the outer arm assembly is connected to the standing column, and the inner arm assembly is connected to the outer arm assembly and the sliding block, and the inner arm assembly and the outer arm assembly are allowed to move relative to each other, wherein the inner arm assembly comprises an inner arm first motor, a transmission assembly, a transmission cylinder, a supporting bearing assembly, an inner arm first connecting rod, an inner arm second motor, an inner arm second connecting rod, an inner arm third motor, and an inner arm third connecting rod;

the inner arm first motor is arranged on the sliding block, the inner arm first motor is connected to the transmission cylinder through the transmission assembly, the transmission cylinder is connected to a first end of the inner arm first connecting rod, and a second end of the inner arm first connecting rod is connected to a first end of the inner arm second connecting rod, a second end of the inner arm second connecting rod is connected to a first end of the inner arm third connecting rod, and a second end of the inner arm third connecting rod is a second clamping end, and the inner arm second motor is arranged at the first end of the inner arm second connecting rod; the inner arm third motor is arranged on the first end of the inner arm third connecting rod; and the transmission cylinder is connected to the sliding block through the supporting bearing assembly, the transmission cylinder is hollow, and the transmission shaft of the outer arm assembly passes through the transmission cylinder.

7. The bi-planar robotic arm device according to claim 6, wherein the transmission assembly comprises a driving pulley, a belt, and a driven pulley, wherein the driving pulley is connected to the inner arm first motor, the driven pulley is coaxially arranged on the transmission cylinder, and the driving pulley is connected to the driven pulley through the belt.

8. The bi-planar robotic arm device according to claim 6, wherein the transmission cylinder coincides with an axis of the transmission shaft of the outer arm assembly, and the transmission cylinder and the transmission shaft of the outer arm assembly are allowed to slide and rotate relative to each other along the axis.

9. The bi-planar robotic arm device according to claim 6, wherein the transmission cylinder rotates under an action of the inner arm first motor and the transmission assembly to drive the inner arm first connecting rod to rotate, and the inner arm first connecting rod is rotatably connected to the inner arm second connecting rod, the inner arm second connecting rod is allowed to rotate relative to the inner arm first connecting rod under an action of the inner arm second motor, and the inner arm second connecting rod is rotatably connected to the inner arm third connecting rod; the inner arm third connecting rod is allowed to rotate relative to the inner arm second connecting rod under an action of the inner arm third motor;
- a rotation axis of the inner arm first connecting rod, a rotation axis of the inner arm second connecting rod, and a rotation axis of the inner arm third connecting rod are parallel to each other;
- the inner arm first connecting rod, the inner arm second connecting rod, and the inner arm third connecting rod are located in a second motion plane.

10. A bi-planar robotic arm device for vascular interventional surgery comprising an operating table, a frame assembly, an outer arm assembly, and an inner arm assembly; the frame assembly comprises a standing column, a sliding block, a sliding platform, a support, and a screw stepper motor;

the standing column is arranged on the operating table, the support is arranged on the standing column, and the sliding platform is arranged on the support, and the sliding platform is connected to the sliding block, the sliding block is connected to the screw stepper motor and is allowed to slide along the sliding platform under an action of the screw stepper motor; and the outer arm assembly is connected to the standing column, and the inner arm assembly is connected to the outer arm assembly and the sliding block, and the inner arm assembly and the outer arm assembly are allowed to move relative to each other, wherein the outer arm assembly comprises an outer arm first motor, a transmission shaft, an outer arm first connecting rod, an outer arm second motor, an outer arm second connecting rod, an outer arm third motor, and an outer arm third connecting rod; and the outer arm first motor is arranged on the standing column, the outer arm first motor is connected to a first end of the outer arm first connecting rod through the transmission shaft, and a second end of the outer arm first connecting rod is connected to a first end of the outer arm second connecting rod, a second end of the outer arm second connecting rod is connected to a first end of the outer arm third connecting rod, a second end of the outer arm third connecting rod is a first clamping end, and the outer arm second motor is arranged at the first end of the outer arm second connecting rod; the outer arm third motor is arranged at the first end of the outer arm third connecting rod, wherein the transmission shaft is a telescopic rod.

* * * * *